US009624328B2

(12) United States Patent
Won et al.

(10) Patent No.: US 9,624,328 B2
(45) Date of Patent: Apr. 18, 2017

(54) SUPERABSORBENT POLYMER

(71) Applicant: LG CHEM, Ltd., Seoul (KR)

(72) Inventors: Tae Young Won, Daejeon (KR); Dae Woo Nam, Daejeon (KR); Chang Sun Han, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

(21) Appl. No.: 14/440,246

(22) PCT Filed: Apr. 28, 2014

(86) PCT No.: PCT/KR2014/003730
§ 371 (c)(1),
(2) Date: May 1, 2015

(87) PCT Pub. No.: WO2014/178588
PCT Pub. Date: Nov. 6, 2014

(65) Prior Publication Data
US 2015/0315321 A1 Nov. 5, 2015

(30) Foreign Application Priority Data

Apr. 30, 2013 (KR) .................. 10-2013-0048744
Apr. 28, 2014 (KR) .................. 10-2014-0050417

(51) Int. Cl.
| C08F 220/06 | (2006.01) |
| C08J 3/24 | (2006.01) |
| C08F 222/10 | (2006.01) |
| A61L 15/22 | (2006.01) |
| A61L 15/60 | (2006.01) |
| C08J 3/075 | (2006.01) |
| C08L 101/14 | (2006.01) |

(52) U.S. Cl.
CPC ........ *C08F 222/1006* (2013.01); *A61L 15/22* (2013.01); *A61L 15/60* (2013.01); *C08F 220/06* (2013.01); *C08J 3/075* (2013.01); *C08J 3/245* (2013.01); *C08L 101/14* (2013.01); *B01J 2220/68* (2013.01); *C08F 2222/1013* (2013.01); *C08J 2300/14* (2013.01)

(58) Field of Classification Search
CPC ........ C08J 3/243; C08J 3/245; C08J 2333/02; C08J 2300/14; C08F 220/06; C08F 222/02; C08F 222/1006; C08F 22/02
USPC ..................... 525/329.7; 526/317.1
See application file for complete search history.

(56) References Cited

U.S. PATENT DOCUMENTS

| 4,734,478 A | 3/1988 | Tsubakimoto et al. |
| 5,140,076 A | 8/1992 | Hatsuda et al. |
| 5,451,613 A * | 9/1995 | Smith ............... A61F 13/15203 |
| | | 521/149 |
| 5,599,335 A * | 2/1997 | Goldman ............... A61L 15/42 |
| | | 604/368 |
| 6,620,889 B1 | 9/2003 | Mertens et al. |
| 7,285,599 B2 | 10/2007 | Mertens et al. |
| 7,285,615 B2 | 10/2007 | Adachi et al. |
| 7,488,535 B2 | 2/2009 | Ehrnsperger et al. |
| 7,510,988 B2 | 3/2009 | Wada et al. |
| 7,833,624 B2 | 11/2010 | Harren et al. |
| 2002/0128618 A1* | 9/2002 | Frenz ..................... A61L 15/60 |
| | | 604/368 |
| 2004/0039360 A1 | 2/2004 | Ehrnsperger et al. |
| 2004/0106745 A1* | 6/2004 | Nakashima ............. A61L 15/60 |
| | | 525/418 |
| 2005/0049379 A1 | 3/2005 | Adachi et al. |
| 2007/0244283 A1 | 10/2007 | Riegel et al. |
| 2008/0125533 A1 | 5/2008 | Riegel et al. |
| 2009/0131255 A1 | 5/2009 | Ikeuchi et al. |
| 2010/0016522 A1* | 1/2010 | Stueven .................. C08F 6/008 |
| | | 526/60 |
| 2012/0035294 A1 | 2/2012 | Kim et al. |
| 2012/0157634 A1 | 6/2012 | Lopez Villanueva |

FOREIGN PATENT DOCUMENTS

| CA | 2433044 A1 | 7/2002 |
| CN | 1482924 A | 3/2004 |
| CN | 1597787 A | 3/2005 |
| CN | 1678358 A | 10/2005 |
| CN | 102471394 A | 5/2012 |
| CN | 102482370 A | 5/2012 |
| JP | 56-161408 A | 12/1981 |
| JP | 57-158209 | 9/1982 |
| JP | 57-198714 | 12/1982 |

(Continued)

OTHER PUBLICATIONS

International Search Report for Application No. PCT/KR2014/003730 dated Aug. 27, 2014.
"Hansen Solubility Parameters in Practice," Hansen-Solubility.com 2013.
"Directory of Solvents." Blackie Academic & Professional, 1996, pp. 22-29.
Industrial Solvents Handbook, Marcel Dekker, Inc., 1996, pp. 35-68.
George Odian, "Principles of Polymerization." Second Edition, John Wiley & Sons, Inc., 1981, p. 203.
Reinhold Schwalm, "UV Coatings: Basics, Recent Developments and New Applications." Elsevier, 2007, p. 115.

(Continued)

*Primary Examiner* — Roberto Rabago
(74) *Attorney, Agent, or Firm* — Lerner, David, Littenberg, Krumholz & Mentlik, LLP

(57) ABSTRACT

The present invention relates to a superabsorbent polymer which has excellent initial absorbency and keeps water from flowing out under pressure even after passage of time. The superabsorbent polymer of the present invention is characterized by simultaneously optimizing centrifuge retention capacity (CRC), absorbency under pressure (AUP), liquid permeability (SFC), and gel strength within a predetermined range. The present invention can provide improved physical properties of a final diaper product and apply an ultra-thin technology to the diaper product.

10 Claims, No Drawings

(56) References Cited

FOREIGN PATENT DOCUMENTS

| JP | 2005097593 A | 4/2005 |
|---|---|---|
| JP | 2005536292 A | 12/2005 |
| JP | 4436686 B2 | 3/2010 |
| JP | 2013503214 A | 1/2013 |
| KR | 100067962 | 11/1993 |
| KR | 20030068198 A | 8/2003 |
| KR | 20070083761 A | 8/2007 |
| KR | 20120081113 A | 7/2012 |
| WO | 95026209 A1 | 10/1995 |
| WO | 02100451 A2 | 12/2002 |
| WO | 2005027986 A1 | 3/2005 |
| WO | 2007116778 A1 | 10/2007 |

OTHER PUBLICATIONS

J.M. Coulson, et. al., "Chemical Enginnering." vol. II, 1978, Pergamon Press, pp. 125-127.
"Absorbency." Textile Science and Technology 7, Elsevier, 1985, pp. 42-43.
Extended Search Report from European Application No. 14 79 2045, dated Sep. 15, 2015.

\* cited by examiner

SUPERABSORBENT POLYMER

CROSS-REFERENCE TO RELATED APPLICATION

This application is a national phase entry under 35 U.S.C. §371 of International Application No. PCT/KR2014/003730, filed Apr. 28, 2014, which claims priority to Korean Patent Application No. 10-2013-0048744, filed Apr. 30, 2013 and Korean Patent Application No. 10-2014-0050417, filed Apr. 28, 2014, the disclosures of which are incorporated herein by reference.

TECHNICAL FIELD

The present invention relates to a superabsorbent polymer which has excellent initial absorbency and keeps water from flowing out under pressure even after passage of time.

BACKGROUND

A superabsorbent polymer (SAP) is a type of synthetic polymeric material capable of absorbing moisture from 500 to 1000 times its own weight. Various manufacturers have denominated it under different names such as SAM (Super Absorbent Material), AGM (Absorbent Gel Material), etc. Since such superabsorbent polymers started to be practically applied in sanitary products, now they are widely used not only for hygiene products such as disposable diapers for children, etc., but also for water retaining soil products for gardening, water stop materials for civil engineering and construction, sheets for raising seedling, fresh-keeping agents for food distribution fields, materials for poultices, or the like.

As a preparation process for such superabsorbent polymers, a process of reverse phase suspension polymerization and a process of solution polymerization have been known. For example, Japanese Patent Laid-open Publication Nos. S56-161408, S57-158209, and S57-198714 disclose the reverse phase suspension polymerization.

The process of solution polymerization further includes a thermal polymerization method in which a polymerization gel is polymerized while being broken and cooled in a kneader equipped with a plurality of shafts, and a photo-polymerization method in which an aqueous solution at a high concentration is irradiated with UV rays onto a belt to be polymerized and dried at the same time.

The water-containing gel polymers thus obtained through the polymerization reaction are generally marketed in a powdery form after drying and pulverization processes.

In the products made of superabsorbent polymers, liquid permeability is an index of determining fluidity of a liquid to be absorbed. Permeability may differ depending on the properties such as particle size distribution of crosslinked polymers, particle shape, and connectedness of open pores, as well as surface modification of the swollen gel. Fluidity of the liquid passing through swollen particles differs depending on permeability of the superabsorbent polymer composition. A liquid cannot flow readily through a superabsorbent polymer with low permeability.

As one of the methods of increasing permeability of the superabsorbent polymer, there is a method of performing a surface crosslinking reaction after polymerization, in which silica or clay is added together with a surface crosslinking agent. For example, U.S. Pat. Nos. 5,140,076 and 4,734,478 disclose the addition of silica during surface crosslinking of dry superabsorbent polymer powders.

However, while permeability is improved by the addition of silica or clay, there are problems that water retention capacity or absorbency under pressure is reduced in proportion thereto, and separation from the superabsorbent polymer easily occurs by external physical impact during transport.

SUMMARY OF THE INVENTION

The present invention provides a superabsorbent polymer which has excellent physical properties, in particular, excellent initial absorbency by surface treatment thereof, and keeps water from flowing out under pressure even after passage of a long period of time to show excellent absorbency.

The present invention provides a superabsorbent polymer, of which centrifuge retention capacity (CRC) for a physiological saline solution is 28 g/g or more, absorbency under pressure (AUP) of 0.7 psi for the physiological saline solution is 22 g/g or more, liquid permeability (SFC) is $20 \times 10^{-7}$ cm$^3$*sec/g or more, and gel strength is 7000 to 11,000 Pa.

In the present invention, the superabsorbent polymer may include a crosslinked polymer which is obtained by surface crosslinking of a powdery base polymer using one or more selected from the group consisting of a substance satisfying $\delta_p < 12$ (J/cm$^3$)$^{1/2}$, a substance satisfying $4 < \delta_H < 6$ (J/cm$^3$)$^{1/2}$, and a substance satisfying $\delta_{tot} > 31$ (J/cm$^3$)$^{1/2}$, $\delta_p$, $\delta_H$, and $\delta_{tot}$ being defined as Hansen solubility parameters, in which the powdery base polymer is prepared by polymerizing water-soluble ethylene-based unsaturated monomers having acidic groups which are at least partially neutralized, using one or more internal crosslinking agents selected from the group consisting of a di(meth)acrylate of a polyol having 2 to 20 carbon atoms and a poly(meth)acrylate of a polyol having 2 to 20 carbon atoms.

The water-soluble ethylene-based unsaturated monomer may be one or more selected from the group consisting of an anionic monomer or salts thereof, a nonionic hydrophilic monomer, and an amino group-containing unsaturated monomer or a quaternary compound thereof, and in which the anionic monomer is acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid; the nonionic hydrophilic monomer is (meth)acrylamide, N-substituted (meth)acrylate, 2-hydroxyethyl(meth)acrylate, 2-hydroxypropyl(meth)acrylate, methoxy polyethylene glycol(meth)acrylate, or polyethylene glycol(meth)acrylate; and the amino group-containing unsaturated monomer is (N,N)-dimethylaminoethyl(meth)acrylate or (N,N)-dimethylaminopropyl(meth)acrylate.

Further, in the present invention, the internal crosslinking agent may be one or more selected from the group consisting of polyethylene glycol diacrylate, glycerin diacrylate, glycerin triacrylate, and trimethylol triacrylate.

In the present invention, the substance satisfying $\delta_p < 12$ (J/cm$^3$)$^{1/2}$ may be one or more selected from the group consisting of ethylene glycol, 1,4-butanediol, 1,6-hexandiol, propylene glycol, 1,2-hexandiol, 1,3-hexandiol, 2-methyl-1,3-propanediol, 2,5-hexandiol, 2-methyl-1,3-pentanediol, 2-methyl-2,4-pentanediol, tripropylene glycol, and glycerol. The substance satisfying $4 < \delta_H < 6$ (J/cm$^3$)$^{1/2}$ may be one or more selected from the group consisting of ethylene carbonate and propylene carbonate. In addition, the substance satisfying $\delta_{tot}>31$ $(J/cm^3)^{1/2}$ may be one or more selected from the group consisting of ethylene glycol, 1,3-propanediol, and glycerol.

In the superabsorbent polymer of the present invention, the centrifuge retention capacity (CRC) for the physiological saline solution may be represented by the following Equation 1.

$$CRC(g/g)=\{[W_2(g)-W_1(g)]/W_0(g)\}-1 \qquad \text{[Equation 1]}$$

In Equation 1, $W_0(g)$ is the weight (g) of the absorbent polymer, $W_1(g)$ is the weight of the apparatus which is measured after draining water off at 250 G for 3 minutes with a centrifuge using no absorbent polymer, and $W_2(g)$ is the weight of the apparatus including the absorbent polymer which is measured after immersing the absorbent polymer in the physiological saline solution at 0.9% by weight at room temperature for 30 minutes and draining water off at 250 G for 3 minutes with a centrifuge.

Further, in the superabsorbent polymer of the present invention, the absorbency under pressure (AUP) of 0.7 psi for the physiological saline solution may be represented by the following Equation 2.

$$AUP(g/g)=[W_4(g)-W_3(g)]/W_0(g) \qquad \text{[Equation 2]}$$

In Equation 2, $W_0(g)$ is the weight (g) of the absorbent polymer, $W_3(g)$ is the total weight of the absorbent polymer and the apparatus capable of providing a load for the absorbent polymer, and $W_4(g)$ is the total weight of the water-absorbed absorbent polymer and the apparatus capable of providing a load for the absorbent polymer, which are measured after supplying water for the absorbent polymer under a load (0.7 psi) for 1 hour.

DETAILED DESCRIPTION OF THE EMBODIMENT

Hereinafter, the superabsorbent polymer and the preparation method thereof will be described in more detail according to specific embodiments of the present invention. However, these are for illustrative purposes only, and the scope of the present invention is not intended to be limited thereby. It will be apparent to those skilled in the art that various modifications may be made thereto without departing from the scope of the invention.

Additionally, the term "including" or "containing" means including a particular component (or particular element) without particular limitations unless otherwise mentioned in the present entire disclosure, and it cannot be interpreted as excluding the addition of the other components.

The present inventors studied a superabsorbent polymer which has excellent initial absorbency and keeps water from flowing out under pressure even after passage of a long period of time so as to show excellent absorbency. As a result of the study, they found that the specific properties of the superabsorbent polymer, for example, centrifuge retention capacity (CRC), absorbency under pressure (AUP), liquid permeability (SFC), and gel strength, are optimized within a predetermined range at the same time to improve physical properties of a final diaper product and apply an ultra-thin technology to the diaper product. The present invention is completed from the above studies.

According to one embodiment of the invention, the present invention provides a superabsorbent polymer which has excellent initial absorbency and keeps water from flowing out under pressure even after passage of a long period of time so as to show excellent absorbency. The super absorbent polymer of the present invention has the specific properties within a predetermined range at the same time, of which centrifuge retention capacity (CRC) for a physiological saline solution is 28 g/g or more, absorbency under pressure (AUP) of 0.7 psi for the physiological saline solution is 22 g/g or more, liquid permeability (SFC) is $20\times10^{-7}$ cm$^3$*sec/g or more, and gel strength is 7000 to 11,000 Pa.

In particular, the superabsorbent polymer of the present invention exhibits the properties of excellent water retention capacity and liquid permeability by performing polymerization using a crosslinking agent having two or more (meth) acrylate groups binding to a polyol, for example, polyethylene glycol diacrylate, as an internal crosslinking agent and by optimizing the type of the surface crosslinking agent and/or the temperature condition of the surface crosslinking reaction within a specific range, as described below. Therefore, the superabsorbent polymer of the present invention, which satisfies the specific parameter properties, can be widely used for various hygiene products. Also, the superabsorbent polymer of the present invention can be used for water-retaining soil products for gardening, water stop materials for civil engineering and construction, sheets for raising seedling, fresh-keeping agents for food distribution fields, materials for poultices, or the like.

As described above, the present invention provides a synergistic effect by physical property combination of optimizing centrifuge retention capacity (CRC), absorbency under pressure (AUP), liquid permeability (SFC), and gel strength of the superabsorbent polymer at the same time. Therefore, the present invention can induce excellent physical properties and a comfortable wearing sensation during manufacture of the absorber.

For the superabsorbent polymer of the present invention, the centrifuge retention capacity (CRC) for the physiological saline solution may be represented by the following Equation 1.

$$CRC(g/g)=\{[W_2(g)-W_1(g)]/W_0(g)\}-1 \qquad \text{[Equation 1]}$$

In Equation 1, $W_0(g)$ is the weight (g) of the absorbent polymer, $W_1(g)$ is the weight of the apparatus which is measured after draining water off at 250 G for 3 minutes with a centrifuge using no absorbent polymer, and $W_2(g)$ is the weight of the apparatus including the absorbent polymer, which is measured after immersing the absorbent polymer in the physiological saline solution at room temperature for 30 minutes and draining water off at 250 G for 3 minutes with a centrifuge. Here, the concentration of the physiological saline solution is 0.9% by weight.

For the superabsorbent polymer, the centrifuge retention capacity (CRC) for the physiological saline solution may be 28 g/g or more, or 28 g/g to 32 g/g, preferably 28.5 g/g or more, and more preferably 29 g/g or more. If the centrifuge retention capacity (CRC) for the physiological saline solution is less than 28 g/g, there is a problem that absorbency of the diaper is reduced.

Further, in the superabsorbent polymer of the present invention, the absorbency under pressure (AUP) of 0.7 psi for the physiological saline solution may be represented by the following Equation 2.

$$AUP(g/g)=[W_4(g)-W_3(g)]/W_0(g) \qquad \text{[Equation 2]}$$

In Equation 2, $W_0(g)$ is the weight (g) of the absorbent polymer, $W_3(g)$ is the total weight of the absorbent polymer and the apparatus capable of providing a load for the absorbent polymer, and $W_4(g)$ is the total weight of the water-absorbed absorbent polymer and the apparatus capable of providing a load for the absorbent polymer, which are measured after supplying water to the absorbent polymer under a load (0.7 psi) for 1 hour.

For the superabsorbent polymer, the absorbency under pressure (AUP) of 0.7 psi for the physiological saline solution may be 22 g/g or more, or 22 g/g to 26 g/g, preferably 23 g/g or more, and more preferably 24 g/g or more. If the absorbency under pressure (AUP) of 0.7 psi for the physiological saline solution is less than 22 g/g, there is a problem that absorbency of the diaper is reduced under pressure.

In the present invention, $W_0(g)$ described in Equations 1 to 2 corresponds to the weight (g) of the absorbent polymer, which is applied to each of the physical properties, and may be the same as or different from each other.

For the superabsorbent polymer of the present invention, the liquid permeability (SFC) may be measured according to Darcy's law and the stationary-flow method (e.g. refer to "Absorbency", edited by P. K. Chatterjee, Elsevier 1985, pp. 42-43 and Chemical Engineering, Vol. II, 3rd edition, J. M. Coulson and J. F. Richarson, Pergamon Press, 1978, pp. 125-127). In the superabsorbent polymer, the liquid permeability (SFC) of 0.7 psi for the physiological saline solution may be $20 \times 10^{-7}$ cm$^3$*sec/g or more, or $20 \times 10^{-7}$ to $50 \times 10^{-7}$ cm$^3$*sec/g, preferably $22 \times 10^{-7}$ cm$^3$*sec/g or more, and more preferably $25 \times 10^{-7}$ cm$^3$*sec/g or more. If the liquid permeability (SFC) of 0.7 psi for the physiological saline solution is less than $20 \times 10^{-7}$ cm$^3$*sec/g, there is a problem that the absorbency of the diaper is reduced under pressure.

Further, the gel strength of the superabsorbent polymer may be 7000 to 11,000 Pa, preferably 7500 to 10,800 Pa, and more preferably 7800 to 10,500 Pa. In the superabsorbent polymer of the present invention, the range of gel strength is optimized in order to obtain a synergistic effect in which centrifuge retention capacity (CRC), absorbency under pressure (AUP), and liquid permeability (SFC) are excellent at the same time. Therefore, the superabsorbent polymer having excellent water retention capacity and liquid permeability can be prepared.

Meanwhile, the superabsorbent polymer of the present invention may include a crosslinked polymer which is obtained by surface crosslinking of a powdery base polymer using a specific surface crosslinking agent. The powdery base polymer is prepared by polymerizing water-soluble ethylene-based unsaturated monomers having acidic groups which are at least partially neutralized, using a specific internal crosslinking agent. In particular, the base polymer is preferably surface-crosslinked according to the present invention since the crosslinking density of the crosslinked polymer may be a factor to affect the absorbency under pressure (AUP).

The water-soluble ethylene-based unsaturated monomer may be one or more selected from the group consisting of an anionic monomer such as acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, and salts thereof; a nonionic hydrophilic monomer such as (meth)acrylamide, N-substituted (meth)acrylate, 2-hydroxyethyl (meth)acrylate, 2-hydroxypropyl(meth)acrylate, methoxy polyethylene glycol(meth)acrylate, or polyethylene glycol (meth)acrylate; and an amino group-containing unsaturated monomer such as (N,N)-dimethylaminoethyl(meth)acrylate or (N,N)-dimethylaminopropyl(meth)acrylate, and a quaternary compound thereof.

Further, the water-soluble ethylene-based unsaturated monomer may be polymerized using an internal crosslinking agent to be a powdery base polymer. The internal crosslinking agent may be a crosslinking agent, which has one or more of the functional group capable of reacting with a water-soluble substituent of the water-soluble ethylene-based unsaturated monomer and has one or more ethylenic unsaturated groups; or a crosslinking agent which has two or more of the functional group capable of reacting with a water-soluble substituent of the monomer and/or a water-soluble substituent formed by hydrolysis of the monomer.

In the illustrated embodiments, the internal crosslinking agent may include a crosslinking agent having two or more (meth)acrylate groups binding to a polyol, for example, a di(meth)acrylate of a polyol having 2 to 20 carbon atoms, a poly(meth)acrylate of a polyol having 2 to 20 carbon atoms, etc. Specifically, the internal crosslinking agent may be one or more selected from the group consisting of polyethylene glycol diacrylate, glycerin diacrylate, glycerin triacrylate, and trimethylol triacrylate.

Further, the superabsorbent polymer of the present invention may include a crosslinked polymer resulting from surface crosslinking of the base polymer which is prepared by polymerizing the water-soluble ethylene-based unsaturated monomers using an internal crosslinking agent such as polyethylene glycol diacrylate, etc. The surface crosslinking agent applied to the base polymer may be one or more selected from the group consisting of a substance satisfying $\delta_p<12$ (J/cm$^3$)$^{1/2}$, a substance satisfying $4<\delta_H<6$ (J/cm$^3$)$^{1/2}$, and a substance satisfying $\delta_{tot}>31$ (J/cm$^3$)$^{1/2}$, $\delta_p$, $\delta_H$, and $\delta_{tot}$ being defined as Hansen solubility parameters.

The substance satisfying $\delta_p<12$ (J/cm$^3$)$^{1/2}$ may be one or more selected from the group consisting of ethylene glycol, 1,4-butanediol, 1,6-hexandiol, propylene glycol, 1,2-hexandiol, 1,3-hexandiol, 2-methyl-1,3-propanediol, 2,5-hexandiol, 2-methyl-1,3-pentanediol, 2-methyl-2,4-pentanediol, tripropylene glycol, and glycerol. Here, ethylene glycol, 1,4-butanediol, propylene glycol, 2-methyl-1,3-propanediol, 2-methyl-1,3-pentanediol, 2-methyl-2,4-pentanediol, or tripropylene glycol may be preferred.

Further, the substance satisfying $4<\delta_H<6$ (J/cm$^3$)$^{1/2}$ may be one or more selected from the group consisting of ethylene carbonate and propylene carbonate. The substance satisfying $\delta_{tot}>31$ (J/cm$^3$)$^{1/2}$ may be one or more selected from the group consisting of ethylene glycol, 1,3-propanediol, and glycerol.

According to another embodiment of the invention, the present invention provides a method for preparing the superabsorbent polymer as described above. The method for preparing the superabsorbent polymer may include the steps of performing thermal polymerization or photopolymerization of a monomer composition containing the water-soluble ethylene-based unsaturated monomer, a polymerization initiator, and the internal crosslinking agent so as to form a water-containing gel polymer; drying the water-containing gel polymer; pulverizing the dried polymer; and adding the surface crosslinking agent to the pulverized polymer to perform the surface crosslinking reaction.

Particularly, according to the present invention, the superabsorbent polymer of the present invention having the excellent water retention capacity and liquid permeability can be prepared by performing polymerization using an internal crosslinking agent such as polyethylene glycol diacrylate and by optimizing the type of the surface crosslinking agent and/or the temperature condition of the surface crosslinking reaction within a specific range, as described below. Thus, the present invention provides a synergistic effect by physical property combination of optimizing centrifuge retention capacity (CRC), absorbency under pressure (AUP), liquid permeability (SFC), and gel strength of the superabsorbent polymer at the same time.

In the process for preparing the superabsorbent polymer of the present invention, the specific crosslinking agent as described above may be used as an internal crosslinking agent. It was already described, and thus its additional description will be omitted. Additionally, as described above, the surface crosslinking reaction may be performed using one or more selected from the group consisting of a substance satisfying $\delta_p<12$ $(J/cm^3)^{1/2}$, a substance satisfying $4<\delta_H<6$ $(J/cm^3)^{1/2}$, and a substance satisfying $\delta_{tot}>31$ $(J/cm^3)^{1/2}$, $\delta_p$, $\delta_H$, and $\delta_{tot}$ being defined as Hansen solubility parameters, as a surface crosslinking agent.

According to the preparation method of the superabsorbent polymer, a superabsorbent polymer which has improved liquid permeability and improved physical properties without a reduction in water retention capacity or absorbency under pressure can be prepared.

Further, in the process for preparing the superabsorbent polymer of the present invention, the monomer composition which is a raw material of the superabsorbent polymer includes the water-soluble ethylene-based unsaturated monomer and the polymerization initiator.

As the water-soluble ethylene-based unsaturated monomer, any monomer which is typically used in the preparation of the superabsorbent polymer may be used without limitation. The water-soluble ethylene-based unsaturated monomer may be any one or more monomers selected from the group consisting of an anionic monomer and salts thereof, a nonionic hydrophilic monomer, and an amino group-containing unsaturated monomer and a quaternary compound thereof.

In particular, the water-soluble ethylene-based unsaturated monomer may be any one or more selected from the group consisting of an anionic monomer such as methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid, and salts thereof; a nonionic hydrophilic monomer such as (meth)acrylamide, N-substituted (meth)acrylate, 2-hydroxyethyl(meth)acrylate, 2-hydroxypropyl(meth)acrylate, methoxy polyethylene glycol(meth)acrylate, or polyethylene glycol(meth)acrylate; and an amino group-containing unsaturated monomer such as (N,N)-dimethylaminoethyl (meth)acrylate or (N,N)-dimethylaminopropyl(meth)acrylate, and a quaternary compound thereof.

More preferably, acrylic acid or a salt thereof, for example, acrylic acid or an alkali metal salt such as a sodium salt thereof, may be used. It is possible to prepare a superabsorbent polymer having excellent physical properties by using these monomers. When the alkali metal salt of acrylic acid is used as the monomer, acrylic acid may be used after being neutralized with a basic compound such as caustic soda (NaOH).

The concentration of the water-soluble ethylene-based unsaturated monomer may be about 20% to about 60% by weight, preferably about 40% to about 50% by weight, based on the monomer composition containing the raw materials of the superabsorbent polymer and a solvent. Also, the concentration of the water-soluble ethylene-based unsaturated monomer may be properly controlled considering polymerization time and reaction conditions. However, if the monomer concentration is too low, the yield of the superabsorbent polymer may become low and an economic problem may occur. On the contrary, if the concentration is too high, process problems such as precipitation of the monomers or deterioration of pulverization efficiency for the polymerized water-containing gel polymer may occur and the physical properties of the superabsorbent polymer may decline In the preparation method of the superabsorbent polymer of the present invention, the polymerization initiator used in polymerization is not particularly limited, as long as it is generally used in the preparation of the superabsorbent polymer.

Specifically, the polymerization initiator may be a thermal polymerization initiator or a photo-polymerization initiator polymerized by UV irradiation, depending on a polymerization method. However, even though the photo-polymerization is performed, a certain amount of heat is generated by UV irradiation or the like and is also generated with an exothermic polymerization reaction. Therefore, the thermal polymerization initiator may be further included.

As the photo-polymerization initiator, a compound capable of forming radicals by light such as UV may be used without limitations in the constitution.

For example, one or more selected from the group consisting of benzoin ether, dialkyl acetophenone, hydroxyl alkylketone, phenyl glyoxylate, benzyl dimethyl ketal, acyl phosphine, and α-aminoketone may be used as the photo-polymerization initiator. Meanwhile, as the specific example of acyl phosphine, commercialized Lucirin TPO, namely, 2,4,6-trimethyl-benzoyl-trimethyl phosphine oxide, may be used. More various photo-polymerization initiators are well disclosed in "UV Coatings: Basics, Recent Developments and New Application (Elsevier, 2007)" written by Reinhold Schwalm, p. 115, however, they are not limited to the above-described examples.

The concentration of the photo-polymerization initiator may be about 0.01% to about 1.0% by weight, based on the monomer composition. If the concentration of the photo-polymerization initiator is too low, the polymerization rate may become low. If the concentration of the photo-polymerization initiator is too high, the molecular weight of the superabsorbent polymer may be decreased and physical properties may not be uniform.

Further, one or more selected from the group consisting of persulfate-based initiators, azo-based initiators, hydrogen peroxide, and ascorbic acid may be used as the thermal polymerization initiator. Specific examples of the persulfate-based initiators may include sodium persulfate ($Na_2S_2O_8$), potassium persulfate ($K_2S_2O_8$), ammonium persulfate (($NH_4)_2S_2O_8$) or the like. Examples of the azo-based initiators may include 2,2-azobis(2-amidinopropane)dihydrochloride, 2,2-azobis-(N,N-dimethylene)isobutyramidine dihydrochloride, 2-(carbamoylazo)isobutylonitril, 2,2-azobis(2-[2-imidazolin-2-yl]propane)dihydrochloride, 4,4-azobis-(4-cyanovaleric acid), or the like. More various thermal polymerization initiators are well-disclosed in 'Principle of Polymerization (Wiley, 1981)' written by Odian, p. 203, however, they are not limited to the above-described examples.

The concentration of the thermal polymerization initiator may be about 0.001% to about 0.5% by weight, based on the monomer composition. If the concentration of the thermal polymerization initiator is too low, additional thermal polymerization hardly occurs, and thus the addition effect of the thermal polymerization initiator is not sufficiently obtained. If the concentration of the thermal polymerization initiator is too high, the molecular weight of the superabsorbent polymer may be decreased and physical properties may not be uniform.

Further, the above-described internal crosslinking agent may be used in the monomer composition, and such internal crosslinking agent is included at a concentration of about 0.01% to about 0.8% by weight based on the monomer composition so as to crosslink the polymerized polymer. For example, the internal crosslinking agent may be used in an amount of 0.4% or more, with respect to the content of acrylic acid before neutralization.

In the preparation method of the present invention, the monomer composition of the superabsorbent polymer may further include an additive such as a thickener, a plasticizer, a preservation stabilizer, an antioxidant, etc., if necessary.

The raw materials such as the above-described water-soluble ethylene-based unsaturated monomer, photo-polymerization initiator, thermal polymerization initiator, internal crosslinking agent, and additive may be prepared in the form of a solution of the monomer composition which is dissolved in a solvent.

A solvent capable of dissolving the above ingredients may be used as the solvent without limitations in the constitution. For example, the solvent may be one or more selected from water, ethanol, ethylene glycol, diethylene glycol, triethylene glycol, 1,4-butanediol, propylene glycol, ethylene glycol monobutyl ether, propylene glycol monomethyl ether, propylene glycol monomethyl ether acetate, methyl ethyl ketone, acetone, methyl amyl ketone, cyclohexanone, cyclopentanone, diethylene glycol monomethyl ether, diethylene glycol ethylether, toluene, xylene, butyrolactone, carbitol, methyl cellosolve acetate, and N,N-dimethylacetamide.

The solvent may be included in an amount excluding the above-described components from the total weight of the monomer composition.

Meanwhile, the method for forming a water-containing gel polymer by thermal polymerization or photo-polymerization of the monomer composition is not particularly limited in the constitution, as long as it is a method typically used.

Specifically, the polymerization method is largely classified into the thermal polymerization and the photo-polymerization according to the polymerization energy source, and the thermal polymerization may be carried out in a reactor like a kneader equipped with agitating spindles and the photo-polymerization may be carried out in a reactor equipped with a movable conveyor belt. The above-described polymerization method is an example only, and the present invention is not limited thereto.

For example, as described above, thermal polymerization is performed by providing hot air to a reactor like a kneader equipped with the agitating spindles or heating the reactor so as to obtain the water-containing gel polymer. The water-containing gel polymer may have a size of centimeters or millimeters when it is discharged from the outlet of the reactor, according to the type of agitating spindles equipped in the reactor. Specifically, the water-containing gel polymer may be obtained in various forms according to the concentration of the monomer composition fed thereto, the feeding speed, or the like, and the water-containing gel polymer having a weight average particle size of 2 to 50 mm can be generally obtained.

Further, as described above, when the photo-polymerization is carried out in a reactor equipped with a movable conveyor belt, the water-containing gel polymer may be obtained in a sheet-type having a width of the belt. The thickness of the polymer sheet may vary according to the concentration of the monomer composition fed thereto and the feeding speed, and the polymer sheet is preferably controlled to have a thickness of about 0.5 to about 5 cm. If the monomer composition is fed so that the thickness of the sheet-type polymer becomes too thin, the production efficiency becomes low, which is not preferred. If the thickness of the sheet-type polymer exceeds 5 cm, the polymerization reaction may not uniformly occur throughout the polymer due to the excessively thick thickness.

The water-containing gel polymer thus obtained by the method may typically have a water content of about 40% to about 80% by weight. Meanwhile, the term "water content", as used herein, means a water content in the total weight of the water-containing gel polymer, which is obtained by subtracting the weight of the dry polymer from the weight of the water-containing gel polymer. Specifically, it is defined as a value calculated by measuring the weight loss according to evaporation of water in the polymer during the drying process by increasing the temperature of the polymer with infrared heating. The water content is measured under the drying conditions determined as follows; the temperature is increased from room temperature to about 180° C. and then the temperature is maintained at 180° C., and the total drying time is determined as 40 minutes, including 5 minutes for the temperature rising step.

Next, the step of drying the water-containing gel polymer thus obtained is performed.

If necessary, a coarsely pulverizing step may be performed before the drying step, in order to increase the efficiency of the drying step.

At this time, an applicable pulverizing device may be included, but the constitution is not limited. Specifically, the pulverizing device may include any one selected from the group consisting of a vertical pulverizer, a turbo cutter, a turbo grinder, a rotary cutter mill, a cutter mill, a disc mill, a shred crusher, a crusher, a chopper, and a disc cutter, but is not limited thereto.

The coarsely pulverizing step may be performed so that the water-containing gel polymer has a particle size of about 2 to about 10 mm.

To pulverize the polymer to have a particle size of less than 2 mm is technically not easy due to its high water content, and agglomeration may occur between the pulverized particles. If the polymer is pulverized to have a particle size of more than 10 mm, the effect of increasing the efficiency in the succeeding drying step may be insignificant.

The water-containing gel polymer coarsely pulverized as above or immediately after polymerization without the coarsely pulverizing step is subjected to a drying process. The drying temperature of the drying step may be about 150 to 250° C. When the drying temperature is lower than 150° C., there is a concern that the drying time becomes excessively long or the physical properties of the superabsorbent polymer finally formed may be deteriorated. On the contrary, when the drying temperature is higher than 250° C., only the surface of the polymer is dried, and thus there is a concern that fine powder may be generated during the subsequent pulverization process and the physical properties of the superabsorbent polymer finally formed may be deteriorated. Therefore, the drying process may be preferably performed at a temperature of about 150 to 200° C., and more preferably about 160 to about 180° C. Thus, the content of the fine powder of 150 μm or less in the final product may be 3% or less, and preferably 2% or less.

Meanwhile, the drying process may be carried out for about 20 to about 90 minutes, considering the process efficiency, but is not limited thereto.

Furthermore, any known drying method may be selected and used in the drying step without limitation in the constitution if it can be generally used for drying the water-containing gel polymer. Specifically, the drying step may be carried out by a method of supplying hot air, irradiating infrared rays, irradiating microwaves, irradiating ultraviolet rays, or the like. When the drying step as above is finished, the water content of the polymer may be about 0.1% to about 10% by weight.

Next, the dried polymer obtained from the drying step is subjected to a pulverization step.

The polymer powder obtained from the pulverization step may have a particle size of about 150 to about 850 μm. Specific examples of a milling device that can be used to pulverize the polymer to have the above particle size may include a pin mill, a hammer mill, a screw mill, a roll mill, a disc mill, a jog mill, or the like, but the present invention is not limited thereto.

The physical properties of the superabsorbent polymer powder finally manufactured after the pulverization step can be properly controlled through a classifying step according to the particle size of the polymer powder obtained from the pulverization. Only a polymer having a particle size of about 150 to about 850 μm is preferably classified and then selectively applied to the surface crosslinking reaction and finally manufactured.

Next, surface crosslinking reaction of the pulverized polymer is performed using one or more selected from the group consisting of a substance satisfying $\delta_p<12$ (J/cm$^3$)$^{1/2}$, a substance satisfying $4<\delta_H<6$ (J/cm$^3$)$^{1/2}$, and a substance satisfying $\delta_{tot}>31$ (J/cm$^3$)$^{1/2}$, $\delta_p$, $\delta_H$, and $\delta_{tot}$ being defined as Hansen solubility parameters.

The surface crosslinking is a step of increasing the crosslinking density in the vicinity of the surface of the superabsorbent polymer particle with regard to the internal crosslinking density of particles. In general, the surface crosslinking agent is applied to the surface of the superabsorbent polymer particle. Therefore, this reaction occurs on the surface of the superabsorbent polymer particle, which improves crosslinking on the surface of the particle without substantially affecting the interior of the particle. Thus, the surface crosslinked superabsorbent polymer particles have a higher level of crosslinking in the vicinity of the surface than in the interior.

According to the present invention, as the surface crosslinking agent, a substance selected from the group consisting of a substance satisfying $\delta_p<12$ (J/cm$^3$)$^{1/2}$, a substance satisfying $4<\delta_H<6$ (J/cm$^3$)$^{1/2}$, and a substance satisfying $\delta_{tot}>31$ (J/cm$^3$)$^{1/2}$, $\delta_p$, $\delta_H$, and $\delta_{tot}$ being defined as Hansen solubility parameters may be used alone or in combinations of two or more thereof.

The substance satisfying $\delta_p<12$ (J/cm$^3$)$^{1/2}$ may be exemplified by ethylene glycol, 1,4-butanediol, 1,6-hexandiol, propylene glycol, 1,2-hexanediol, 1,3-hexanediol, 2-methyl-1,3-propanediol, 2,5-hexanediol, 2-methyl-1,3-pentanediol, 2-methyl-2,4-pentanediol, tripropylene glycol, glycerol, etc. In addition, the substance satisfying $4<\delta_H<6$ (J/cm$^3$)$^{1/2}$ may be exemplified by ethylene carbonate and propylene carbonate. The substance satisfying $\delta_{tot}>31$ (J/cm$^3$)$^{1/2}$ may be exemplified by ethylene glycol, 1,3-propanediol, and glycerol. However, the present invention is not limited thereto, and any substance satisfying the range of the parameter is possible, even though it is not described in the following Table 1.

Hansen solubility parameters were developed by Charles Hansen as a way of predicting if one material will dissolve in another to form a solution. They are parameters described in, for example, [INDUSTRIAL SOLVENTS HANDBOOK] (pp. 35-68, Marcel Dekker, Inc., published in 1996), [DIRECTORY OF SOLVENTS] (pp. 22-29, Blackie Academic & Professional, published in 1996), or the like.

Typically, cohesive energy should be obtained in order to calculate solubility parameters. In Hansen solubility parameters, cohesive energy affecting the solubility parameters is divided into the following three parameters.

$\delta_D$: solubility parameter due to non-polar dispersion energy (unit: (J/cm$^3$)$^{1/2}$)

$\delta_P$: solubility parameter due to dipolar energy (unit: (J/cm$^3$)$^{1/2}$)

$\delta_H$: solubility parameter due to hydrogen bonding energy (unit: (J/cm$^3$)$^{1/2}$)

$$\delta_{tot}:((\delta_D)^2+(\delta_P)^2+(\delta_H)^2)^{1/2}$$

The above parameters are obtained to determine a distance between Hansen solubility parameters of two materials, thereby calculating a similarity in the solubilities of the two materials. For example, if Hansen solubility parameters of A and B are $(\delta_D^A, \delta_P^A, \delta_H^A)$ and $(\delta_D^B, \delta_P^B, \delta_H^B)$, respectively, a distance (Ra) between Hansen solubility parameters of the two materials can be calculated by the following equation.

$$Ra=(4*(\delta_D^A-\delta_D^B)^2+(\delta_P^A-\delta_P^B)^2+(\delta_H^A-\delta_H^B)^2)^{1/2}$$

As the Ra value is larger, it is likely that similarity between two materials is decreased in terms of solubility.

Hansen solubility parameters of several substances applicable as the crosslinking agent were calculated according to HSPiP (Hansen Solubility Parameters in Practice, 3$^{rd}$ edition version 3.1 published by Hansen-Solubility.com) developed by Dr. Hansen's group, as shown in the following Table 1.

TABLE 1

| Substance | Hansen solubility parameter (unit: (J/cm$^3$)$^{1/2}$) | | | |
|---|---|---|---|---|
| | $\delta_D$ | $\delta_P$ | $\delta_H$ | $\delta_{tot}$ |
| ethylene glycol | 17.0 | 11.0 | 26.0 | 33.0 |
| 1,3-propanediol | 16.8 | 13.5 | 23.2 | 31.7 |
| 1,4-butanediol | 16.6 | 11.0 | 20.9 | 28.9 |
| 1,6-hexandiol | 15.7 | 8.4 | 17.8 | 25.2 |
| propylene glycol | 16.8 | 10.4 | 21.3 | 29.1 |
| 1,2-hexanediol | 16.0 | 7.4 | 16.7 | 24.9 |
| 1,3-hexanediol | 16.5 | 8.1 | 20.9 | 27.8 |
| 2-methyl-1,3-propanediol | 16.3 | 9.2 | 22.8 | 29.5 |
| 2,5-hexanediol | 16.0 | 7.5 | 23.9 | 29.7 |
| 2-methyl-1,3-pentanediol | 15.9 | 7.1 | 22.4 | 28.4 |
| 2-methyl-2,4-pentanediol | 16.0 | 8.3 | 22.1 | 28.5 |
| ethylene carbonate | 18.0 | 21.7 | 5.1 | 28.7 |
| propylene carbonate | 20.0 | 18.0 | 4.1 | 27.2 |
| diethylene glycol | 16.6 | 12.0 | 19.0 | 27.9 |
| triethylene glycol | 16.0 | 12.5 | 18.6 | 27.5 |
| tripropylene glycol | 16.0 | 6.8 | 16.3 | 23.8 |
| glycerol | 17.4 | 11.3 | 27.2 | 34.2 |

According to one embodiment of the present invention, the surface crosslinking reaction may be performed by further adding porous silica or clay, together with the surface crosslinking agent.

With regard to the method of adding the surface crosslinking agent to the polymer, there is no limitation in the constitution. A method of adding and mixing the surface crosslinking agent and the polymer powder in a reactor, a method of spraying the surface crosslinking agent onto the polymer powder, or a method of continuously feeding the polymer and the surface crosslinking agent to a mixer which is continuously operated may be used.

When the surface crosslinking agent is added, water and methanol may be mixed and further added. When water and methanol are added, there is an advantage that the surface crosslinking agent can be uniformly dispersed in the polymer. At this time, the content of water and methanol added is preferably about 2 to about 9 parts by weight, and preferably 3 to 7 parts by weight, based on 100 parts by weight of the polymer, in order to induce uniform dispersion of the surface crosslinking agent, to prevent agglomeration of the polymer powder, and to optimize the surface penetration depth of the crosslinking agent.

The surface crosslinking reaction is allowed to occur by heating the surface crosslinking agent-added polymer particles at about 180° C. or higher, or at about 180 to 190° C., for 20 minutes or longer, or for 20 to 40 minutes. The surface crosslinking process may be preferably performed by heating at a temperature of about 180 to about 190° C. for about 30 to about 40 minutes. In particular, the surface crosslinking process of the present invention may be performed under conditions of a maximum reaction temperature of 190 to 200° C. and a total reaction time of 0.5 to 1 hour, and of maintaining the reaction temperature at 180° C. or higher for about 25 minutes or longer. For example, the surface crosslinking reaction step may be performed for 10 minutes to 50 minutes, and preferably 20 minutes to 40 minutes, until the temperature reaches 180° C., and then maintained at 180° C. or higher for 30 minutes to 50 minutes, and preferably 35 minutes to 45 minutes. If the crosslinking reaction temperature is lower than 180° C., much reaction time may be required. If the crosslinking reaction temperature is higher than 200° C., carbonization of the product may occur to produce odor. In addition, if the crosslinking reaction time is as short as less than 20 minutes, sufficient surface crosslinking reaction may not occur. If the crosslinking reaction time is longer than 60 minutes, the polymer particles are damaged due to excessively long surface crosslinking reaction time, leading to deterioration in the physical properties.

A means for raising the temperature for surface crosslinking reaction is not particularly limited. Heating may be performed by providing a heating medium or by directly providing a heat source. The type of the heating medium applicable for surface crosslinking reaction may be a hot fluid such as steam, hot air, hot oil, or the like. However, the present invention is not limited thereto. The temperature of the heating medium may be properly controlled, considering the means of the heating medium, the heating rate, and the target temperature. Meanwhile, an electric heater or a gas heater may be used as the heat source provided directly, but the present invention is not limited to these examples.

The superabsorbent polymer obtained according to the preparation method of the present invention may have improved liquid permeability without deterioration of physical properties such as water retention capacity and absorbency under pressure.

In the present invention, it is possible to add and subtract something other than the above description, if necessary, and thus the present invention is not particularly limited thereto.

Advantageous Effects

According to the present invention, when centrifuge retention capacity (CRC), absorbency under pressure (AUP), liquid permeability (SFC), and gel strength of the superabsorbent polymer are optimized within a predetermined range at the same time, it is possible to improve physical properties of a final diaper product and apply an ultra-thin technology to the diaper product.

In particular, the superabsorbent polymer of the present invention can be applied to production of excellent hygiene products with an easy and comfortable wearing sensation, because it shows a small amount of rewetting even after passage of a predetermined time.

EXAMPLES

Hereinafter, the preferred examples are provided for better understanding. However, the following examples are for illustrative purposes only, and the present invention is not intended to be limited by these examples.

Example 1

A monomer aqueous solution was prepared by mixing 100 g of acrylic acid, 0.5 g of polyethylene glycol diacrylate (Mw=523) as a crosslinking agent, 81.1 g of 50% caustic soda (NaOH), and 97.5 g of water.

Subsequently, 800 g of the monomer aqueous solution was mixed with 56.4 g of 0.26% ascorbic acid solution and 57.4 g of 2.1% sodium persulfate solution, and the mixture was fed through a feed section of a continuous polymerization reactor with a kneader, together with 56.2 g of 0.7% hydrogen peroxide solution, so as to perform polymerization. At this time, temperature of the reactor was maintained at 80° C., the maximum polymerization temperature was 110° C., and the polymerization time was 1 minute and 15 seconds. Thereafter, kneading was continuously performed, and polymerization and kneading were performed for 20 minutes. The polymers having a size of 0.2 cm or less were thus distributed. At this time, the water content of the water-containing gel polymer finally formed was 51% by weight.

Subsequently, the water-containing gel polymer was dried with a hot air dryer of 180° C. for 30 minutes, and the dried water-containing gel polymer was pulverized with a pin mill Next, the polymer was classified into a polymer having a particle size (average particle size) of less than 150 µm and a polymer having a particle size of 150 µm to 850 µm by using a sieve.

Then, the surface treatment solution containing 0.5% by weight of 1.3-propanediol and 0.5% by weight of propylene glycol was sprayed onto the prepared base polymer to perform surface treatment of the superabsorbent polymer. Further, in the surface treatment step, the classified water-containing gel polymers were fed to one surface crosslinking reactor, and then a surface crosslinking reaction of the water-containing gel polymers was performed at 180° C. or higher for 40 minutes. At this time, temperature of the base polymer (Resin) was directly monitored and is shown in Table 2.

After the surface treatment, a surface treated-superabsorbent polymer having an average particle size of 150 to 850 µm was obtained through a process using a sieve. The content of 150 µm or less in a product of the superabsorbent polymer was less than 2%.

Examples 2-4 and Comparative Examples 1-4

Superabsorbent polymers were prepared in the same manner as in Example 1, except that the reaction time, reaction temperature, and heating conditions were changed as shown in the following Table 2.

Experimental Example

Physical properties of the superabsorbent polymers prepared in Examples 1-4 and Comparative Examples 1-4 were evaluated as follows, and then the physical properties thus measured are shown in the following Table 2.

(1) Particle Size

The particle size of the base polymers and the superabsorbent polymers used in Examples 1-4 and Comparative Examples 1-3 was measured according to EDANA WSP 220.2 (European Disposables and Nonwovens Association, EDANA).

(2) Centrifuge Retention Capacity (CRC)

Retention capacity by absorbency under no load was measured for the absorbent polymers of Examples 1-4 and Comparative Examples 1-4 according to EDANA WSP 241.2 (European Disposables and Nonwovens Association, EDANA).

That is, the polymer $W_0$ (g, about 0.2 g) obtained in Examples 1-4 and Comparative Examples 1-4 was uniformly placed into a nonwoven-fabric-made bag, followed by sealing. Then, the bag was immersed in a physiological saline solution at room temperature, of which the concentration of the physiological saline solution was 0.9% by weight. After 30 minutes, the bag was drained at 250 G for 3 minutes with a centrifuge, and the weight $W_2$(g) of the bag was then measured. Further, the same procedure was carried out using no polymer, and the resultant weight $W_1$(g) was measured.

Thus, CRC (g/g) was calculated from these weights thus obtained, according to the following Equation 1 so as to confirm water retention capacity.

$$CRC(g/g)=\{[W_2(g)-W_1(g)]/W_0(g)\}-1 \quad \text{[Equation 1]}$$

In Equation 1, $W_0$(g) is the weight (g) of the absorbent polymer, $W_1$(g) is the weight of the apparatus which is measured after draining water off at 250 G for 3 minutes with a centrifuge using no absorbent polymer, and $W_2$(g) is the weight of the apparatus including the absorbent polymer, which is measured after immersing the absorbent polymer in the physiological saline solution at 0.9% by weight at room temperature for 30 minutes and draining water off at 250 G for 3 minutes with a centrifuge.

(3) Absorbency Under Pressure (AUP)

Absorbency under pressure (AUP) was measured for the superabsorbent polymers of Examples 1-4 and Comparative Examples 1-4 according to EDANA WSP 242.2 (European Disposables and Nonwovens Association, EDANA).

First, a 400 mesh stainless steel net was installed in the bottom of the plastic cylinder having the internal diameter of 60 mm. The polymer $W_0$ (g, 0.90 g) obtained in Examples 1-4 and Comparative Examples 1-4 was uniformly scattered on the steel net at room temperature and humidity of 50%, a piston which can provide a load of 4.83 kPa (0.7 psi) uniformly was put thereon, in which the external diameter of the piston was slightly smaller than 60 mm, there was no gap between the internal wall of the cylinder and the piston, and the jig-jog of the cylinder was not interrupted. At this time, the weight $W_3$(g) of the device was measured.

After putting a glass filter having a diameter of 90 mm and a thickness of 5 mm in a petri dish having the diameter of 150 mm, a physiological saline solution composed of 0.90% by weight of sodium chloride was poured in the dish until the surface level of the physiological saline solution became equal to the upper surface of the glass filter. A sheet of filter paper having a diameter of 90 mm was put thereon. The measuring device was put on the filter paper and the solution was absorbed for 1 hour under the load. After 1 hour, the weight $W_4$(g) was measured after lifting up the measuring device.

The absorbency under pressure was calculated from the weights thus obtained, according to the following Equation 2.

$$AUP(g/g)=[W_4(g)-W_3(g)]/W_0(g) \quad \text{[Equation 2]}$$

In Equation 2, $W_0$(g) is the weight (g) of the absorbent polymer, $W_3$(g) is the total weight of the absorbent polymer and the apparatus capable of providing a load for the absorbent polymer, and $W_4$(g) is the total weight of the water-absorbed absorbent polymer and the apparatus capable of providing a load for the absorbent polymer, which are measured after supplying water for the absorbent polymer under a load (0.7 psi) for 1 hour.

(4) Liquid Permeability (SFC)

Liquid permeability (SFC) was measured for the superabsorbent polymers of Examples 1-4 and Comparative Examples 1-4 according to Darcy's law and the stationary-flow method (e.g., "Absorbency", edited by P. K. Chatterjee, Elsevier 1985, pp. 42-43 and Chemical Engineering, Vol. II, 3rd edition, J. M. Coulson and J. F. Richarson, Pergamon Press, 1978, pp. 125-127).

(5) Gel Strength

Gel strength was measured for the superabsorbent polymers of Examples 1-4 and Comparative Examples 1-4 according to the following method.

First, the polymer samples (30-50 mesh) obtained in Examples 1-4 and Comparative Examples 1-4 were passed through a sieve, and 0.5 thereof was weighed. The sample thus weighed was sufficiently swollen in 50 g of 0.9% NaCl solution for 1 hour. Thereafter, the swollen gel was spread on a Buchner funnel covered with a filter paper to remove excess fluid with vacuum for 3 minutes. The gel was kept in a closed container until ready for testing.

Before placing the gel between the parallel plates of a Rheometer, it was blotted on filter paper to be sure that no free water was present between the particles during testing.

Then, gel strength was measured by using 2 g of the swollen gel with a Rheometer. At this time, the Rheometer was performed under the experimental conditions of Plate Gap Size 2 mm; Strain amplitude 1%; Oscillation frequency 10 radian/sec; ambient temperature 22° C.; plate 25 mm, TA Instruments—AR Series. After measured for 5 minutes, the average value was taken as the measured value.

TABLE 2

|  | Comparative Example 1 | Comparative Example 2 | Comparative Example 3 | Comparative Example 4 | Example 1 | Example 2 | Example 3 | Example 4 |
|---|---|---|---|---|---|---|---|---|
| Reaction time (min) | 4.8 | 14.4 | 24 | 33.6 | 46.4 | 56 | 56 | 56 |
| Maximum reaction temperature (° C.) | 122.2 | 165.7 | 180.4 | 187.4 | 194.2 | 194.2 | 194.2 | 194.2 |
| Heating rate (° C.) | 19.2 | 9.4 | 6.3 | 4.7 | 3.5 | 19.2 | — | — |
| CRC (g/g) | 33.5 | 35 | 35.1 | 32.7 | 30.2 | 30.3 | 30 | 29.9 |
| AUP (g/g) | 7.3 | 8.1 | 13.3 | 24.2 | 25.7 | 25 | 25 | 24.8 |
| SFC ($\times 10^{-7}$ cm$^3$*sec/g) | 0 | 0 | 0 | 8 | 29 | 37 | 35 | 33 |
| Gel strength (Pa) | 6,212 | 5,657 | 6,261 | 7,409 | 8,773 | 8,069 | 8,156 | 8,401 |

As shown in Table 2, the superabsorbent polymers of Examples 1-4 according to the present invention showed improved liquid permeability and excellent absorbency, compared to those of Comparative Examples 1-4, and they can be used to produce diapers in an ultra-thin technology.

The invention claimed is:

1. A superabsorbent polymer, of which centrifuge retention capacity (CRC) for a physiological saline solution is 28 g/g or more, absorbency under pressure (AUP) of 0.7 psi for the physiological saline solution is 22 g/g or more, liquid permeability (SFC) is $25 \times 10^{-7}$ cm$^3$*sec/g or more, and gel strength is 7500 to 10,800 Pa, wherein the superabsorbent polymer includes a powdery base polymer comprising a crosslinked polymer prepared by polymerizing water-soluble ethylene-based unsaturated monomers having acidic groups which are at least partially neutralized; and a surface crosslinking layer comprising a surface crosslinked polymer prepared by further crosslinking the crosslinked polymer of the powdery base polymer which is formed on the powdery base polymer.

2. The superabsorbent polymer of claim 1, wherein the base polymer is crosslinked in the presence of one or more internal crosslinking agents selected from the group consisting of a di(meth)acrylate of a polyol having 2 to 20 carbon atoms and a poly(meth)acrylate of a polyol having 2 to 20 carbon atoms; and the surface crosslinking layer is further crosslinked in the presence of one or more surface crosslinking agents selected from the group consisting of a substance satisfying $\delta_p < 12$ (J/cm$^3$)$^{1/2}$, a substance satisfying $4 < \delta_H < 6$ (J/cm$^3$)$^{1/2}$, and a substance satisfying $\delta_{tot} > 31$ (J/cm$^3$)$^{1/2}$, $\delta_p$, $\delta_H$, and $\delta_{tot}$ being defined as Hansen solubility parameters.

3. The superabsorbent polymer of claim 2, wherein the water-soluble ethylene-based unsaturated monomer is one or more selected from the group consisting of an anionic monomer or salts thereof, a nonionic hydrophilic monomer, and an amino group-containing unsaturated monomer or a quaternary compound thereof, and in which the anionic monomer is acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid; the nonionic hydrophilic monomer is (meth)acrylamide, N-substituted (meth)acrylate, -2-hydroxyethyl(meth)acrylate, 2-hydroxypropyl(meth)acrylate, methoxy polyethylene glycol (meth)acrylate, or polyethylene glycol (meth)acrylate; and the amino group-containing unsaturated monomer is (N,N)-dimethylaminoethyl(meth)acrylate or (N,N)-dimethylaminopropyl (meth)acrylate.

4. The superabsorbent polymer of claim 2, wherein the internal crosslinking agent is one or more selected from the group consisting of polyethylene glycol diacrylate, glycerin diacrylate, glycerin triacrylate, and trimethylol triacrylate.

5. The superabsorbent polymer of claim 2, wherein the substance satisfying $\delta_p < 12$ (J/cm$^3$)$^{1/2}$ is one or more selected from the group consisting of ethylene glycol, 1,4-butanediol, 1,6-hexandiol, propylene glycol, 1,2-hexandiol, 1,3-hexandiol, 2-methyl-1,3-propanediol, 2,5-hexandiol, 2-methyl-1,3-pentanediol, 2-methyl-2,4-pentanediol, tripropylene glycol, and glycerol.

6. The superabsorbent polymer of claim 2, wherein the substance satisfying $4 < \delta_H < 6$ (J/cm$^3$)$^{1/2}$ is one or more selected from the group consisting of ethylene carbonate and propylene carbonate.

7. The superabsorbent polymer of claim 2, wherein the substance satisfying $\delta_{tot} > 31$ (J/cm$^3$)$^{1/2}$ is one or more selected from the group consisting of ethylene glycol, 1,3-propanediol, and glycerol.

8. The superabsorbent polymer of claim 1, wherein the water-soluble ethylene-based unsaturated monomer is one or more selected from the group consisting of an anionic monomer or salts thereof, a nonionic hydrophilic monomer, and an amino group-containing unsaturated monomer or a quaternary compound thereof, and in which the anionic monomer is acrylic acid, methacrylic acid, maleic anhydride, fumaric acid, crotonic acid, itaconic acid, 2-acryloylethane sulfonic acid, 2-methacryloylethane sulfonic acid, 2-(meth)acryloylpropane sulfonic acid, or 2-(meth)acrylamide-2-methyl propane sulfonic acid; the nonionic hydrophilic monomer is (meth)acrylamide, N-substituted (meth)acrylate, 2-hydroxyethyl(meth)acrylate, 2 hydroxypropyl(meth)acrylate, methoxy polyethylene glycol (meth)acrylate, or polyethylene glycol (meth)acrylate; and the amino group-containing unsaturated monomer is (N,N)-dimethylaminoethyl(meth)acrylate or (N,N)-dimethylaminopropyl (meth)acrylate.

9. A method for preparing the superabsorbent polymer of claim 1, including:

the step of performing thermal polymerization or photopolymerization of a monomer composition containing a water-soluble ethylene-based unsaturated monomer, a polymerization initiator, and an internal crosslinking agent to form a water-containing gel polymer;
the step of drying the water-containing gel polymer;
the step of pulverizing the dried polymer; and
the step of adding a surface crosslinking agent to the pulverized polymer to perform a surface crosslinking reaction,
wherein the internal crosslinking agent includes one or more selected from the group consisting of a di(meth)

acrylate of a polyol having 2 to 20 carbon atoms and a poly(meth)acrylate of a polyol having 2 to 20 carbon atoms;

the surface crosslinking agent includes one or more selected from the group consisting of a substance satisfying $\delta_p < 12$ $(J/cm^3)^{1/2}$, a substance satisfying $4 < \delta_H < 6$ $(J/cm^3)^{1/2}$, and a substance satisfying $\delta_{tot} > 31$ $(J/cm^3)^{1/2}$, $\delta_p$, $\delta_H$, and $\delta_{tot}$ being defined as Hansen solubility parameters; and the step of the surface crosslinking reaction is performed under conditions of a maximum reaction temperature of 190 or higher and a total reaction time of 30 minutes or longer, and of maintaining the reaction temperature at 180° C. or higher for about 25 minutes or longer.

10. The superabsorbent polymer of claim 1, wherein the liquid permeability (SFC) ranges from $25 \times 10^{-7}$ to $37 \times 10^{-7}$ $cm^3$*sec/g.

* * * * *